(12) United States Patent
Brielmeier et al.

(10) Patent No.: US 10,412,927 B2
(45) Date of Patent: Sep. 17, 2019

(54) METHOD AND DEVICE FOR IMPROVED HYGIENIC MONITORING IN IVC SYSTEMS

(71) Applicants: TECNIPLAST S.P.A., Buguggiate (IT); HELMHOLTZ ZENTRUM MUNCHEN DEUTSCHES FORSCHUNGSZENTRUM FUR GESUNDHEIT UND UMWELT (GmbH), Neuherberg (DE)

(72) Inventors: Markus Brielmeier, Garching (DE); Wolfgang Nagel, München (DE); Julia Zorn, München (DE); Alfredo Campiotti, II, Buguggiate (IT); Gianpaolo Milite, Udine (IT); Carmelo Di Martino, Gallarate (IT)

(73) Assignees: TECNIPLAST S.P.A., Buguggiate (IT); HELMHOLTZ ZENTRUM MÜNCHEN DEUTSCHES FORSCHUNGSZENTRUM FÜR GESUNDHEIT UND UMWELT (GMBH), Neuherberg (DE)

( * ) Notice: Subject to any disclaimer, the term of this patent is extended or adjusted under 35 U.S.C. 154(b) by 61 days.

(21) Appl. No.: 15/337,599

(22) Filed: Oct. 28, 2016

(65) Prior Publication Data

US 2017/0118949 A1 May 4, 2017

(30) Foreign Application Priority Data

Oct. 30, 2015 (IT) .................. 102015000067602

(51) Int. Cl.
*A01K 1/03* (2006.01)
*C12Q 1/68* (2018.01)
(Continued)

(52) U.S. Cl.
CPC .............. *A01K 1/031* (2013.01); *A01K 29/00* (2013.01); *C12Q 1/6806* (2013.01); *G01N 1/2208* (2013.01); *G01N 1/2247* (2013.01)

(58) Field of Classification Search
CPC ...... A01K 1/031; A01K 29/00; C12Q 1/6806; G01N 1/2208; G01N 1/2247
(Continued)

(56) References Cited

U.S. PATENT DOCUMENTS

| 5,846,487 A | * | 12/1998 | Bennett, II | ............ B01L 3/5085 |
| | | | | 422/417 |
| 2011/0005465 A1 | * | 1/2011 | Tamborini | ............ A01K 1/031 |
| | | | | 119/419 |

(Continued)

OTHER PUBLICATIONS

Search Report for Italian Application Serial No. 102015000067602 dated Jul. 13, 2016, pp. 1-9.

*Primary Examiner* — Jill A Warden
*Assistant Examiner* — Jacqueline Brazin
(74) *Attorney, Agent, or Firm* — Pepper Hamilton LLP (57) ABSTRACT

The present invention concerns a device for improved hygienic monitoring of individually ventilated caging (IVC) rack systems for laboratory animals and method for contamination-free removal of biological samples from unwanted organisms from the IVC-rack system. The device allows the performance of sampling operations on a ventilated shelving system in a safe and effective manner, without interfering with the ventilation air flow. The method of the invention allows the removal and transfer of the biological sample from inside the IVC-rack in a contamination-free manner by enabling a safe transfer of the sample from inside the IVC-rack system to any further processing procedure for analysis of the biological sample outside the IVC-rack system. It is also an object of the present invention to provide a device which is adapted to be used also on existing (Continued)

ventilated shelving systems, allowing the refitting of existing IVC-rack systems.

12 Claims, 9 Drawing Sheets (51) Int. Cl.
  *A01K 29/00*  (2006.01)
  *G01N 1/22*  (2006.01)
  *C12Q 1/6806*  (2018.01)
(58) Field of Classification Search
  USPC .......................................................... 422/500
  See application file for complete search history.

(56) References Cited

U.S. PATENT DOCUMENTS

2011/0239953 A1   10/2011   Tchekneva et al.
2015/0004679 A1*  1/2015   Conger .................. A01K 1/031
                                                            435/287.2

\* cited by examiner

METHOD AND DEVICE FOR IMPROVED HYGIENIC MONITORING IN IVC SYSTEMS

This application claims the benefit of Italian Patent Application Serial No. 102015000067602 filed Oct. 30, 2015, which is hereby incorporated by reference in its entirety.

FIELD

The present invention relates to a device for improved monitoring of the hygienic conditions in IVC (individually ventilated caging) rack systems for laboratory animals, a method for contamination-free removal of biological samples, particularly of unwanted organisms from the IVC rack system for laboratory animals containment cages, and a sampling method for sampling airborne particles in a ventilated shelving storage in order to analyze potential infections of the animals in the IVC rack system.

BACKGROUND

The present invention belongs to the field of hygienic monitoring of animal containment facilities, particularly IVC (individually ventilated cages) rack systems.

Ventilated shelving storage units are currently known and used for housing laboratory animals, said units enabling a plurality of cages containing animals to be arranged in a tidy manner.

It is also well-known, among those skilled in the art, that the shelving storage units of the kind mentioned above also cater for the need to ensure air circulation inside the cages containing the animals, and prevent said air from being released into the atmosphere.

For this purpose, the cages for containing the animals according to the prior art are equipped with at least two valves, one for delivering and one for discharging the air, while the shelving storage unit or rack system comprises at least one line, or plenum for delivering clean air into the containment cages and one line, or plenum for conveying (removing) the foul air away from the cages.

It is moreover well known that particular care must be taken for the purpose of treating the foul air leaving the cage, because same could be contaminated by pathogens contained in the cages. Moreover, the foul air coming from the cages often contains solid substances in the form of airborne particles and/or micro-particles arising from the solid substances and/or from the dust generally existing in the cages.

Still a further issue relates to the fact that the air to be delivered to the cages must be filtered in advance to comply with the required quality standards so as to ensure that the animals are always kept in an environment with controlled characteristics. For this purpose, the cage rack systems are generally fitted with an air circulation system that delivers air to the clean air plenum only after it has been pre-filtered and usually treated with a HEPA (high efficiency particulate air) filter, which is capable of retaining any airborne particles.

However, the use of IVC rack systems in laboratory animal husbandry has posed new challenges relating in particular to effective microbiological monitoring. Generally speaking, monitoring microbiological conditions (in the following "microbiological monitoring" for the sake of conciseness), in particular of SPF (Specific Pathogen Free) animals, is based on international standards, which have been established by scientific societies in the international laboratory science community.

As an example, in Europe and in the United States microbiological monitoring standards are established by the FELASA (Federation of European Laboratory Animals Science Association) and by the ACLAM (American College of Laboratory Animal Medicine), respectively. As it is known, it is very important to prevent entry into the cages and spread among the cages of unwanted infectious agents, such as for example bacteria and viruses, and therefore the use of individually ventilated cage (IVC) rack systems in laboratory animal husbandry has dramatically increased in the last years. In fact, IVCs not only allow for a control of environmental conditions such as humidity and temperature, they also allow to provide each cage with filtered air, which protects the animals in the cages from airborne infectious or other noxious particulate agents present in the environment.

Microbiological monitoring of animals requires a regular analysis for the presence of infectious agents which may be particle-associated or air-borne. In fact, although housing of animals in IVC rack systems reduces the risk of infection from the environment, routine handling operations such as, for example, changing of bedding and experimental handling of animals, (usually carried out in changing stations such as laminar flow hoods or the like), or even in an unprotected environment, still harbors a risk of exposing the animals to environmental conditions and infectious agents and, thus, to infections.

STATE OF THE ART

As stated here above, in the field of cages for animals, an increasing need is felt to monitoring the microbiological conditions of the cages.

In this respect, it has to be noted that each individual cage represents its own zone of bio-containment, so that traditional monitoring methods such as exposure of sentinels to airborne infectious agents present in the room air are inappropriate. In the same way, sampling of random animals from the IVC rack is usually not suitable, as in this case the use of large numbers of potentially valuable animals is required.

Thus, in an attempt to overcome the above mentioned drawbacks, the use of sentinels exposed to soiled bedding has been developed. However, soiled bedding may not detect pathogens not transmitted by the faecal-oral route.

Pathogens can comprise viruses, fungi, bacteria, spores, parasites and similar.

As a further development of traditional methods of microbiological monitoring, the used of sentinels exposed to exhaust air from the entire rack has been suggested. As an example, according to prior art document DE 100 26 208, detection of pathogens is carried out by delivering to at least one cage of sentinel animals samples of the exhaust air coming from the rack. Therefore, the sentinel animals serve as bio-indicators for the detection of air-borne infectious agents which may be present in the air either due to the development of a disease or indirectly due to to the development of antibodies or amplification of pathogens, which may be detected according to either immunological or microbiological methods.

The sentinel-based monitoring system described in DE 100 26 208 is affected by several shortcomings. As a first drawbacks, the sentinel animals have to be sensitive and susceptible to the respective pathogens in order to develop an immune response or disease. In addition, a minimum infectious dose of the respective pathogen has to be present and there may, furthermore, be a substantial time lag for the sentinels to develop a disease, amplify the pathogen and/or develop antibodies. Thus, by the time a pathogen is detected, a large number of affected animals may have been infected and subsequently used in experiments, thus rendering the results as obtained questionable and/or less reliable.

As a further drawbacks, for the purpose of efficiently monitoring different racks at different times a large number of sentinel animals is required. However, to sacrifice a large number of animals merely for health monitoring purposes does not only constitute an enormous financial burden, but represents a less-desirable practice for ethical and animal-welfare reasons.

The international patent application WO2009115220 in the name of the same Applicant discloses a cage rack system and method for sampling airborne particles from a cage rack system suitable to accommodate a plurality of cages, ventilated either individually or in groups, said system being provided with air guidance means for delivering air to the air-inlet and/or collecting air from the air-outlet through integral (common) or separated conduits, wherein at least one sampling unit for collecting airborne particles from the air is further provided.

According to this method, the sampling unit is adapted to collect the airborne particles by means of a cyclonic flow path configured to cause a separation of the particles from the air.

The disclosed sampling unit comprises one or more components, and can be arranged for analyzing, evaluating, investigating, controlling and/or monitoring the incoming air and/or the outgoing air.

The incoming air can be checked in order to have a basis for comparing the respective results with the results from one or more components of the air guidance system analyzing, evaluating, controlling and/or checking the outgoing air. In case one or more animals are infected with pathogens, these pathogens are delivered to the air either by the air exhaled from the animals or by excretions of the animals or even by any other contamination of the air due to at least partially contaminating particles in the exhaust air.

The sampling unit according to WO2009115220 can further comprise at least one cyclone and at least one collection vessel, said one or more vessels being disposed downstream of the cyclone. The cyclone can be established by a plurality, such as two or three, of stages in order to minimize its size and/or enhance its effectiveness. As an alternative or in addition, a plurality of cyclones connected in series or parallel with differently located ports can be connected to the air guidance system.

According to a preferred embodiment disclosed in WO2009115220 the sampling unit can be replaceably attached to and/or inserted into a conduit of the air guidance system.

The conduit can comprise a flange and/or access for the direct attachment or insertion of the sampling unit. The sampling unit can be attachable to and/or into the flange and/or access in an air tight manner, preferably by a snap fit, a coupling ring or a bayonet coupling.

The possibility to detachably associate the sampling unit to a conduit of the air guidance system of the cage rack, is an aspect which is particularly aiming at a modular possibility to detect, analyze, evaluate, control and/or monitor the conditions of a certain cage or common group of cages according to the needs and/or circumstances, wherein said needs may change depending on the specific animals contained in the cages at any given point in time.

The prior international patent application WO2009115220 therefore contemplates the possibility to provide an IVC rack system with a sampling unit, preferably detachably associable to a conduit of the air guidance system of the IVC apparatus, However, the present invention bears some major improvements with regard to the handling and transfer of the biological sample originating from the airflow of inside the IVC-rack system.

An unsolved problem of the disclosed IVC rack system and the respective method for sampling airborne particles from a cage rack system according to WO2009115220 relates to the safety conditions under which samples are drawn from the airflow inside the IVC-system so as to avoid any contamination. In order to safely remove the sampling unit from the conduit system it seems to be mandatory that, during the opening operation the air-flow be stopped in order to avoid contamination both of the operator and the system outside and for the animals inside the IVC-rack system and the sample itself.

Not least, a problem left unsolved by the system and method for sampling airborne particles from a cage shelving system according to the prior art is represented by the fact that it is not possible to provide already existing cage rack systems with the sampling unit, in a very easy and cost-effective manner.

SUMMARY

The main aim of the present invention is therefore that of providing a device for improved hygienic monitoring in IVC-rack systems for laboratory animals and a method for contamination-free removal of biological samples of unwanted organisms from the IVC rack system in order to subsequently analyze potential contaminations from the inside of the IVC rack system.

At the same time, according to the present invention, solutions are provided to overcome further drawbacks left unsolved by the prior art.

It is also an object of the present invention that of providing a ventilated shelving storage system comprising said device according to the invention.

It is a further object of the present invention to provide a device for improved hygienic monitoring in IVC-rack systems for laboratory animals which can be easily and safely handled by the operator without the need to interrupt the rack system ventilation. Likewise, the present invention shall allow the withdrawal of the sample from the air guidance system of the cage rack without disturbance of the existing regular air-flow.

Not least, a further object of the present invention is that of providing a device which can be installed also on already existing cage rack systems, thus enabling the retrofitting of already existing apparatuses.

It is a further object of the invention to enable improvement of hygienic monitoring of colonies of laboratory animals kept in individually ventilated cages. It has been shown that the data generated with the device according to the present invention provide much better information on the health status of the animal colonies. In comparison to the method according to the prior art comprising sentinel animals of the prior art, the data generated with the device and method of the present invention are more sensitive and available in less time. The device and method according to the present invention makes the use of extra animals for hygienic monitoring unnecessary.

In view of the above, in particular in order to achieve both the above aims and further aims that will become more clear from the following detailed description of a preferred embodiment of the present invention as depicted in the drawings to be regarded as an illustrative and not limitative example of the present invention, disclosed in the present application is a device for contamination-free removal of biological samples from a ventilated shelving storage system for laboratory animals containment cages, comprising
 a support frame, and sampling means, in turn comprising a capturing scaffold and capturing means arranged within a capturing portion of said capturing scaffold.

As further disclosed, said sampling means may be associated in a removable manner with the support frame.

As further disclosed said support frame may comprise one or more seats for receiving one or more sampling means and at least one aperture adjacent to said one or more seats.

Still as disclosed, said sampling means may comprise a sheath, a capturing scaffold associated to said sheath, and a capturing means associated to said capturing portion.

As further disclosed, said capturing scaffold may be inserted into the sheath and be movable in a sliding manner with respect to the sheath to a capturing position located in the aperture, between a closed position in which said capturing portion containing the capturing means is completely inserted into the sheath and, an open position in which said capturing portion containing the capturing means is completely exposed to the air flow, comprising the area of the aperture not covered by the capturing portion and the flow passage area of the ventilated shelving storage system.

Still as disclosed, one or more seats for receiving sampling means may be delimited by guiding means, so that each sampling means can be slidingly inserted into a dedicated seat.

As further disclosed, said guiding means may comprise straight and elongated guides, each seat being delimited by a couple of straight and elongated guides.

As disclosed, said support frame may comprise a substantially planar plate with a substantially rectangular profile comprising a first short edge, a second short edge, a first long edge and a second long edge connecting said short edges.

As disclosed, said support frame may further comprise at least one flow passage area and/or said sheath and said capturing scaffold may are made of disposable material.

Further disclosed is a ventilated shelving storage system for laboratory animals containment cages comprising a load-bearing structure for supporting a plurality of cages and an air guidance means comprising a filtering unit, said system comprising a device as disclosed above.

As disclosed, the device may be associated in a removable manner to said filtering unit (305).

Still as disclosed, said filtering unit may comprise a containment case and said support frame system of said sampling collection device may be configured to be inserted in a sliding manner into said containment case.

According to the disclosure, said filtering unit comprise a pre-filter and said device is inserted into said filtering unit underneath said pre-filter.

Further disclosed is a method for contamination-free removal of biological samples from a ventilated shelving storage system for laboratory animals containment cages by means of a device according to the above, the method comprising the following steps:
 providing a sampling means for said device,
 positioning of the sampling means of said device from the closed position to the open position,
 collecting of biological samples from unwanted organisms,
 positioning of the sampling means of said device from the open position to the closed position,
 pulling off the sampling means from the filtering unit,
 transferring the sampling means to a ventilated hood,
 shifting the capturing scaffold, comprising the capturing means to the open position,
 transferring the capturing means to a reaction vessel for analysis of biological samples of unwanted organisms, preferably by PCR.

Still in view of the above, according to an embodiment of the present invention there is provided a device for contamination-free removal of biological samples from a ventilated shelving storage system for laboratory animals containment cages, said device comprising—a support frame, and sampling means in turn comprising a capturing scaffold, and capturing means arranged within a capturing portion of said capturing scaffold, said sampling means comprising a sheath, said capturing scaffold being associated to said sheath, said capturing scaffold being inserted into the sheath and movable in a sliding manner with respect to the sheath to a capturing position located in an aperture, between a closed position in which said capturing portion (containing the capturing means) is completely inserted into the sheath, and an open position in which said capturing portion is completely exposed to the an air flow, comprising the area of the aperture not covered by the capturing portion and the flow passage area of the ventilated shelving storage system.

According to an embodiment, said sampling means is associated in a removable manner with the support frame.

According to an embodiment, said support frame comprises one or more seats for receiving one or more of said sampling means, said aperture being adjacent to said one or more seats.

According to an embodiment, said one or more seats for receiving said sampling means are delimited by guiding means so that each sampling means can be slidingly inserted into a dedicated seat.

According to an embodiment, said guiding means comprise straight and elongated guides, each seat being delimited by a couple of straight and elongated guides.

According to an embodiment, said support frame comprises a substantially planar plate with a substantially rectangular profile comprising a first short edge, a second short edge, a first long edge and a second long edge connecting said short edges.

According to an embodiment, said support frame further comprises at least one flow passage area.

According to an embodiment, said sheath and said capturing scaffold are made of disposable material.

According to the present invention there is further provided a ventilated shelving storage system for laboratory animals containment cages comprising a load-bearing structure for supporting a plurality of cages and an air guidance means comprising a filtering unit, said system comprising a device according to any one of the above embodiments.

According to an embodiment, the device is associated in a removable manner to said filtering unit.

According to an embodiment, said filtering unit comprises a containment case and said support frame system of said sampling collection device is configured to be inserted in a sliding manner into said containment case.

According to an embodiment, said filtering unit comprises a pre-filter and said device is inserted into said filtering unit underneath said pre-filter.

According to the present invention there is further provided a method for contamination-free removal of biological samples from a ventilated shelving storage system for laboratory animals containment cages by means of a device according to one of the above embodiments, said method comprising the following steps:
 providing a sampling means for said device, positioning (moving) the sampling means of said device from the closed position to the open position,
collecting biological samples from unwanted organisms,
positioning (moving) the sampling means of said device from the open position to the closed position,
pulling off the sampling means from the filtering unit,
transferring the sampling means to a ventilated hood,
shifting the capturing scaffold, comprising the capturing means to the open position,
transferring the capturing means to a reaction vessel for analysis of biological samples of unwanted organisms, preferably by PCR.

BRIEF DESCRIPTION OF THE DRAWINGS

Further characteristics and advantages of the present invention will become clear from the following detailed description of the embodiments of the present invention depicted in the drawings; however, the present invention is not limited to the embodiments disclosed in the following and depicted in the drawings but comprises all equivalents thereof which may be obvious to those skilled in the art in view of the following disclosure.

In the drawings.

DETAILED DESCRIPTION

With reference to the above mentioned Figures, the main task of the present invention is to provide a device for contamination-free removal of biological samples from a ventilated shelving storage system for laboratory animals containment cages.

The device 10 for contamination-free removal of biological samples particularly from unwanted organisms from a ventilated shelving storage system 100 for laboratory animals containment cages 200 according to an embodiment the present invention comprises a support frame 11, a sampling means 20, for the analysis of the unwanted organisms captured by the capturing means 23, which is arranged within the capturing portion 24 of a capturing scaffold (support) 22.

Contamination-free according to the present application has to be understood as meaning that only material coming from the cages with the animals that is transported via the foul air is captured by the capturing means, whilst no material from outside the air system of the cage rack system can be captured by the capturing means. In this way, wrong (i.e. positive but false) results are avoided.

Contamination-free also means that the personnel taking the sample is not contaminated by potentially dangerous biological material from the animals in the cage rack system. The capturing means is only exposed to biological material from the cages when it is in its operating position inside the filtering unit. Outside the operating position the capturing means is covered by the sheath in order to prevent both contamination of the sample and contamination of the personnel.

Unwanted organisms in the sense of the invention comprise small parasitic animals or single cell parasites including their eggs and larvae, bacteria, fungi, viruses or prions and other biological pathogens.

Biological samples are entire organisms or parts of them like cellular organelles or macromolecules like polypeptide, nucleic acids, lipids, carbohydrates or small molecules.

The capturing means is designed to collect from the foul air flowing through the filtering unit biological materials. In this respect the capturing means might be a membrane, tissue, sponge, swab, paper, grid or any other useful structure made of organic or synthetic material like cotton, cellulose or synthetics or metal. Also electronic devices such as sensors or microchips might be used as the capturing means. The capturing means might be covered by an adhesive in order to better collect biological materials.

Figure 1:
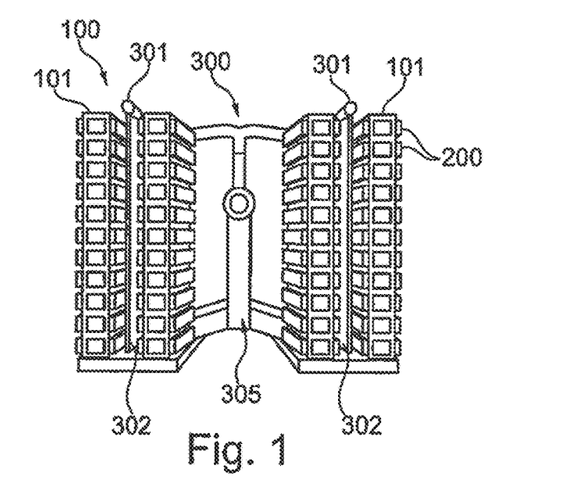
FIG. 1 shows an example of ventilated cage rack or shelving system.

With reference to FIG. 1, a ventilated cage rack system 100 is disclosed in the following.

According to a preferred embodiment of the present invention, a ventilated shelving storage system 100 for laboratory animals containment cages 200 comprises a load-bearing structure 101 for supporting a plurality of cages 200 and an air guidance means 300 comprising a filtering unit 305. The ventilated shelving storage system according to the invention further comprises the device 10.

This is further illustrated in the above-mentioned figures as a non-limiting example, wherein the ventilated shelving system 100 comprises a load-bearing structure 101 suitable for supporting in a tidy array a plurality of cages 200 for containing laboratory animals.

The cage shelving system further comprises air guidance means 300 comprising at least an air supply duct 301 for supplying clean air to the cages 200 and an air return duct 302 for collecting exhaust air coming from the cages 200.

Said air guidance means 300 of the ventilated rack system are preferably in communication with the centralized heating ventilation and air conditioning (HVAC) system, so that the air supplied to the air guidance means 300 is clean air coming from the centralized HVAV system.

Similarly, a plurality of vertical ducts for the air discharged from the cages 200 convey the foul air from the cages into the return exhaust air duct 302.

Again with reference to FIG. 1, the air guidance means 300 further comprise a filtering unit 305 which filters the air coming from the ventilated cages 200.

As shown in FIG. 1, the filtering unit 305 preferably comprises a box-shaped containment structure or case 306 advantageously fitted with a removable wall to give ready access to one or more filter elements contained inside the containment case 306.

The filter element, or each of the filter elements if there is more than one, advantageously consists of a frame supporting a material suitable for filtering the particles contained in the foul air.

The shape and the degree of separation of the filter elements can vary according to need, depending on the size of the ventilated shelving storage system, the level of pollution predicted in the air and various other parameters, based on experience.

Figure 1A:
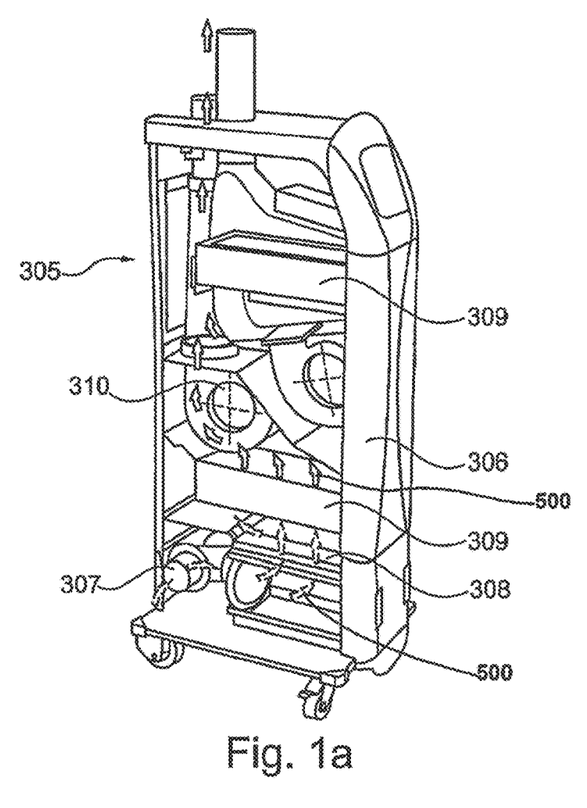
FIG. 1a shows a scheme of the air filtering unit of the ventilated cage shelving system of FIG. 1.

With reference to FIG. 1a, an example of a typical air filtering unit 305 of a ventilated shelving system of the type considered herewith is shown.

The air filtering unit 305 preferably comprises a containment case 306, an inlet duct 307 connected to the plenum 302 through which the exhaust air coming from the cages 200 is fed to the filter unit, a pre-filter 308 and an HEPA filter 309.

The air coming from the inlet duct 307 is moved by a fan 310, the air passes through the pre-filter 308 and then through the HEPA filter 309.

Figure 2:
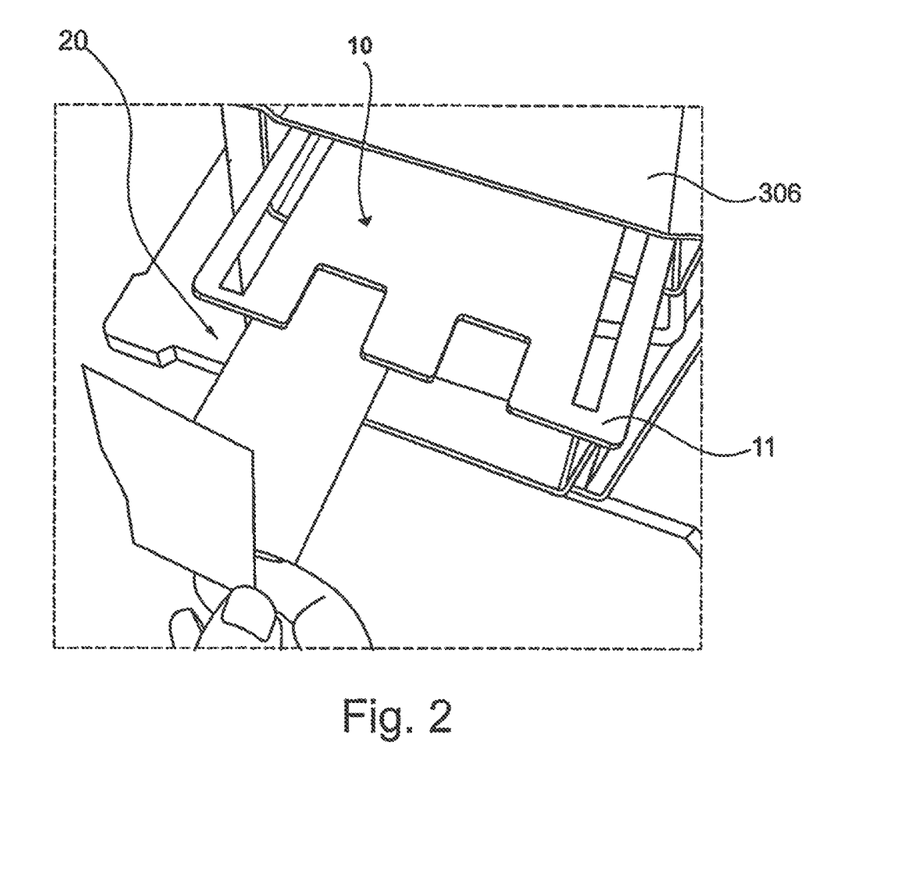
FIG. 2 shows the device according to the present invention partially inserted in the filtering unit of the air guidance means of the shelving system.
Figure 2A:
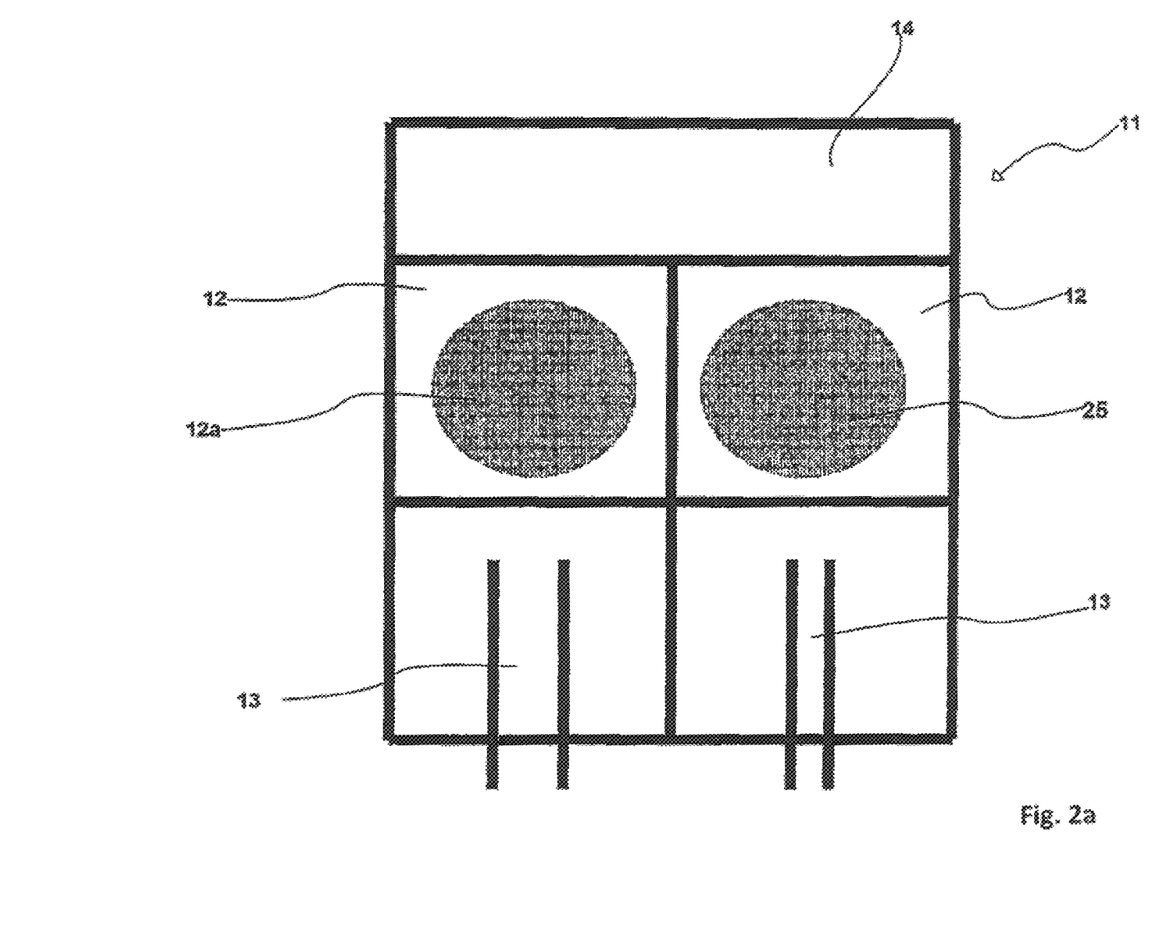
FIG. 2a shows a schematic representation of a support frame as part of the device according to the present invention.

As to a device 10 according to the general concept of the present invention, FIG. 2a shows an example thereof. The support frame 11 as part of the device 10 according to the present invention is shown. The support frame 11 is adapted to reversibly hold said sampling means 20 by means of the guiding means 13 thus allowing to positioning the capturing means 23 at a preferred capturing position 25 which is situated within an aperture 12 provided on the support frame system 11. Furthermore, in FIG. 2b an example at the general concept of sampling means 20 as part of the device 10 is shown. The sampling means comprises the capturing means 23 supported by a capturing scaffold (support) 22, and the capturing sheath 21.

Figure 2B:
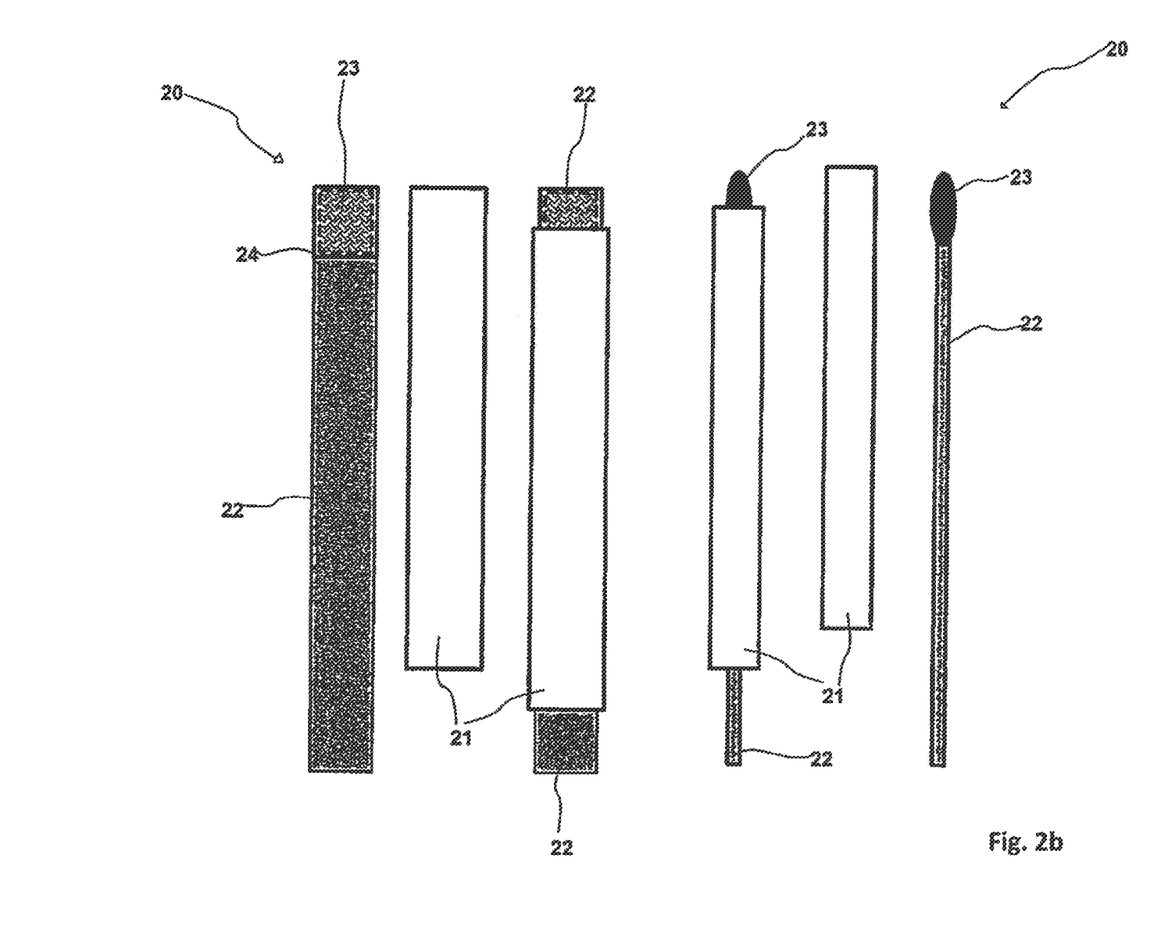
FIG. 2b shows a schematic representation of two alternative embodiments of the sampling means of the device according to the present invention, in particular having respectively a flat and a cylindrical configuration.
Figure 2C:
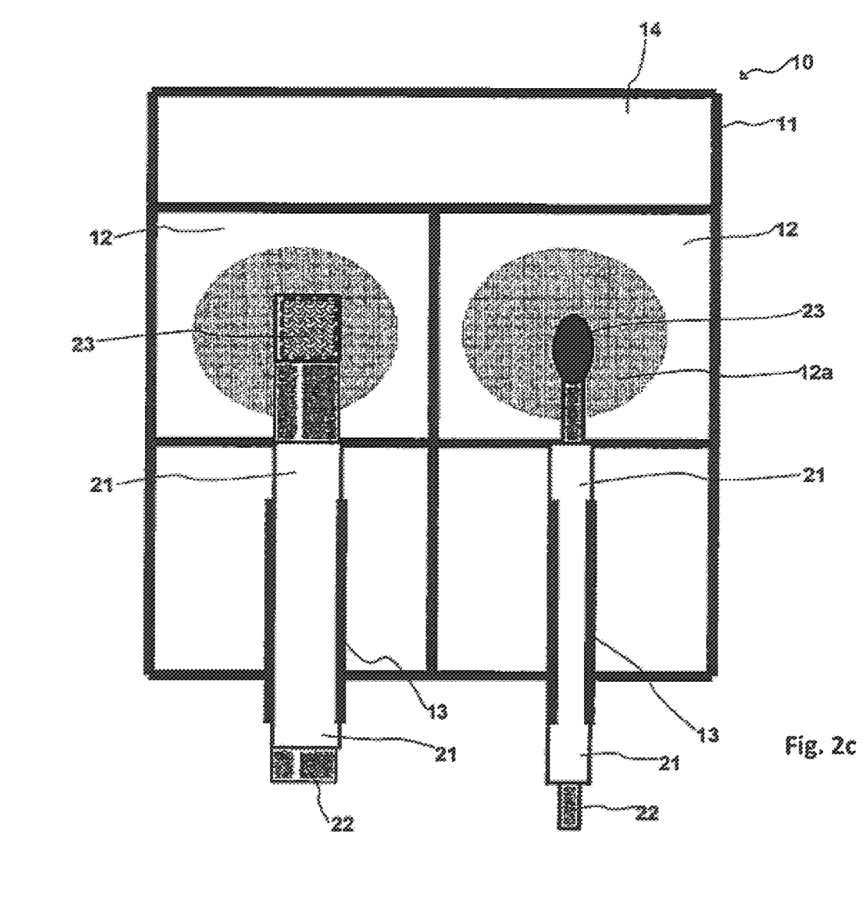
FIG. 2c shows a schematic representation of a device according to the present invention comprising the support frame and the sampling means reversibly connected to each other.

With reference to FIG. 2c an example of the device 10 comprises the support frame 11 and sampling means 20 as shown in FIGS. 2a and 2b is shown. With respect to the sampling means 20 FIGS. 2b and 2c. The guiding means could as well be a tubular structure guiding a cylindrical capturing scaffold with a cylindrical or spheroidal capturing means in a sliding manner. The frame might hold several tubular guiding means arranged side by side in a parallel fashion in order to cover several positions within the aperture.

According to a preferred embodiment of the device 10 according to the present invention, said capturing scaffold 22 is inserted into the sheath 21 and is suitable to be moved in a sliding manner with respect to the sheath 21 to a capturing position 25 located in the aperture 12, between a closed position in which said capturing portion 24 containing the capturing means 23 is completely inserted into the sheath 21 and, an open position in which said capturing portion 24 containing the capturing means 23 is completely exposed to the air flow, comprising the area of the aperture 12 not covered by the capturing portion 24 and the flow passage area 14 of the ventilated shelving storage system 100.

Sliding in the sense of the invention means easily movable within a conducting structure like a rail, a groove or the like.

With reference to FIG. 2d, a preferred embodiment of the device 10 according to the present invention is shown. More particularly, FIG. 2d shows how the device 10 is inserted into/removed from the filtering unit 305.

According to a further embodiment of the invention the filtering unit 305 comprises a containment case 306 wherein said support frame 11 of said sampling collection device 10 is configured to be inserted in a sliding manner into said containment case 306.

Additionally, the filtering unit 305 of the ventilated shelving storage system of the resent invention comprises a pre-filter 308, said device 10 being inserted into said filtering unit 305 underneath said pre-filter 308.

In more detail, the device 10 according to the present invention is preferably inserted into the filtering unit 305 underneath the pre-filter 308, thus capturing particles of the potentially contaminated air coming from the plenum 302 and entering the inlet duct 307.

Said device which is preferably a planar plate is also insertable underneath the pre-filter of filtering units of existing ventilated shelving storage systems produced in the past and already provided to research laboratories. Therefore, the technology object of the present invention as described herewith can also be used in association with all ventilated shelving systems having said filtering units of the kind delivered to the market in the past. The possibility of retrofitting allows all users of such ventilated shelving systems to take advantage of the new technology.

According to a preferred embodiment of the present invention the sampling means 20 is associated in a removable manner with the support frame 11.

Figure 3:
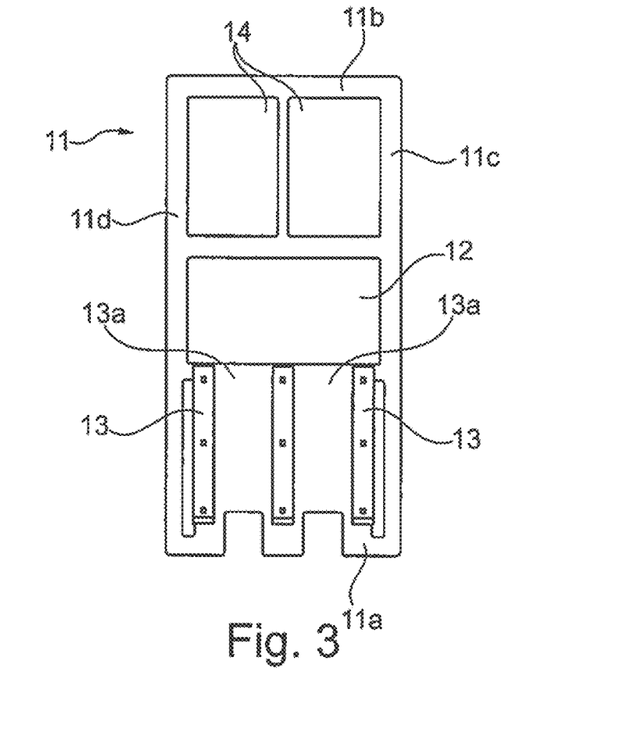
FIG. 3 is a bottom view of the support frame which is part of the device according to the present invention.
Figure 4:
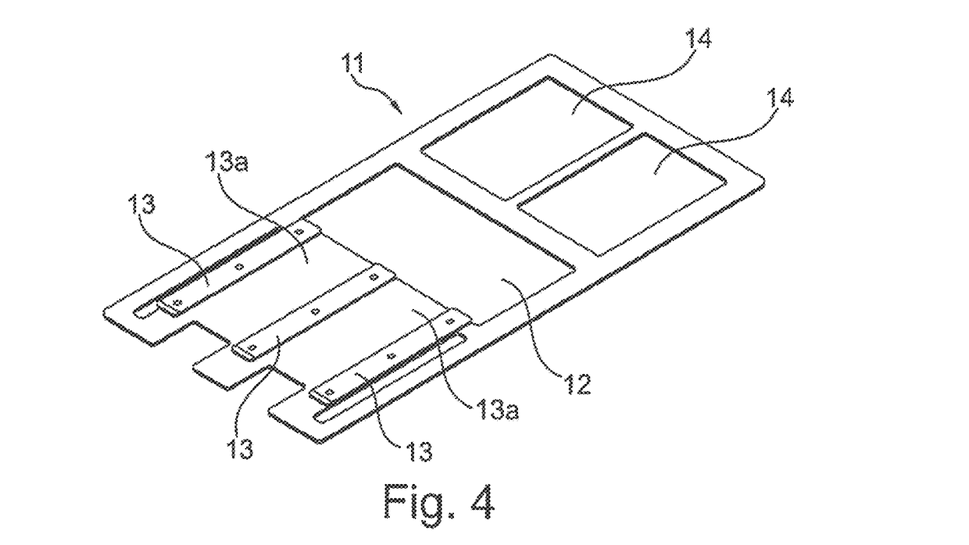
FIG. 4 shows a perspective bottom view of the support frame of FIG. 3.

With reference to FIGS. 3 and 4, the device 10 according to the present invention advantageously comprises a support frame 11 which is configured to be removably inserted into the containment case 306 of said filtering unit 305.

According to a preferred embodiment of the present invention the device 10 is associated in a removable manner to said filtering unit 305 of the ventilated shelving storage system 100.

According to the present invention said filtering unit 305 preferably comprises a containment case 306, and said support frame 11 of said sampling collection device 10 is configured to be inserted in a sliding manner into said containment case 306.

As shown in FIG. 2, said support frame 11 is configured to be slidingly inserted into and or removed from the containment case 306 of the filtering unit 305.

According to a preferred embodiment of the present invention the ventilated shelving storage system 100 comprises a filtering unit 305 in turn comprising a pre-filter 308, said device 10 being inserted into said filtering unit 305 underneath said pre-filter 308.

According to a preferred embodiment of the present invention the support frame 11 comprises one or more seats 13a for receiving one or more sampling means 20 and further comprises at least one aperture 12 adjacent to said one or more seats 13a.

Preferably, said sampling means 20 comprises a sheath 21, a capturing scaffold 22 associated to said sheath 21, and a capturing means 23 associated to the capturing portion 24 of said capturing scaffold 22.

According to FIGS. 3 and 4, depicting a preferred embodiment of the present invention, when the containment case 306 is substantially box-shaped, with a rectangular horizontal cross-section, the support frame 11 of the device 10 advantageously is a substantially planar plate with a substantially rectangular profile.

The support frame 11 is further provided with at least one aperture 12.

According to a preferred embodiment said guiding means 13 comprise straight and elongated plates, each seat 13a being delimited by a couple of straight and elongated plates.

According to a preferred embodiment the support frame 11 comprises a substantially planar plate with a substantially rectangular profile comprising a first short edge 11a, a second short edge 11b, a first long edge 11c and a second long edge 11d connecting said short edges 11a, 11b.

According to a preferred embodiment said support frame 11 further comprises at least one flow passage area 14.

With reference to FIG. 2, the support frame 11 is conceived in order to be inserted with its second short edge 11b positioned forward, so that the said second short edge 11b is the first to enter the containment case 306.

The other, first short edge 11a, is therefore facing the outside of the containment case 306 of the filtering unit 305 once the support frame 11 is inserted therein.

According to FIGS. 3 and 4, the support frame 11 is provided with at least one aperture 12.

In more detail, when the support frame 11 is inserted into said containment case 306 of said filtering unit 305 said aperture 12 is positioned where the air of the inlet duct 307 enters the pre-filter. This is the preferred capturing position 25 to collect airborne particles from the foul air.

In any case, said at least one aperture 12 defines an area which, once the supporting frame 11 is in its open position, i.e. completely inserted into the containment case 306 of the filtering unit 305, is entirely passed by part of the air flow which goes through the filtering unit 305.

Preferably, and according to the preferred technical characteristics of the filtering unit 305, said support frame 11 further comprises at least a flow passage area 14 provided close to the second short edge 11b of said support frame 11, so that once the support frame 11 is completely inserted into the containment case 306 of the filtering unit 305, and therefore it is in its operative position, the air flowing into the filtering unit can freely pass through the said at least one flow passage 14, so that the air flow which goes through the filtering unit 305 is not negatively affected by the presence of the device 10.

When two apertures 12 are provided on said supporting frame 11, once the supporting frame 11 is completely inserted into the containment case 306 of the filtering unit 305, and therefore it is in its operative position, a proportion of the air flowing into the filtering unit will flow through the entire area of both said apertures 12.

The device 10 according to the present invention further comprises sampling means 20.

The support frame 11 is configured to support said sampling means 20 by a guiding means 13.

In more detail, sampling means 20 are associated in a removable manner to said support frame 11. Preferably, according to the preferred embodiment shown in FIGS. 3 and 4, the support frame 11 is provided with guide means 13 so that said sampling means 20 can be inserted into the support frame 11 in a sliding manner guided by said guiding means 13, that defines a seat 13a for receiving said sampling means 20.

Preferably, said guiding means 13 comprises straight and elongated plates arranged parallel to each other and parallel to the short edges 11a, 11b of the frame 11. Two parallel plates define a seat 13a. The guiding means 13 could also be formed like a tube guiding a sampling means 20 that is cylindrically shaped.

According to the example disclosed herewith, the support frame 11 is provided with two seats 13a, positioned side by side on said frame, for receiving two of said sampling means 20. Said at least one seat 13a for receiving said at least one sampling means 20 is provided on the support frame 11 adjacent to said at least one aperture 12.

The possibility to insert more than one sampling means 20 at the same time on the support frame 11 allows the technician to perform a different laboratory test on each sampling means 20.

Having more than one samples allows to test overlapping time periods. Additionally, it allows to retain a so called back-up sample in case the primary sample is lost for example in the analyzing laboratory.

Figure 5:
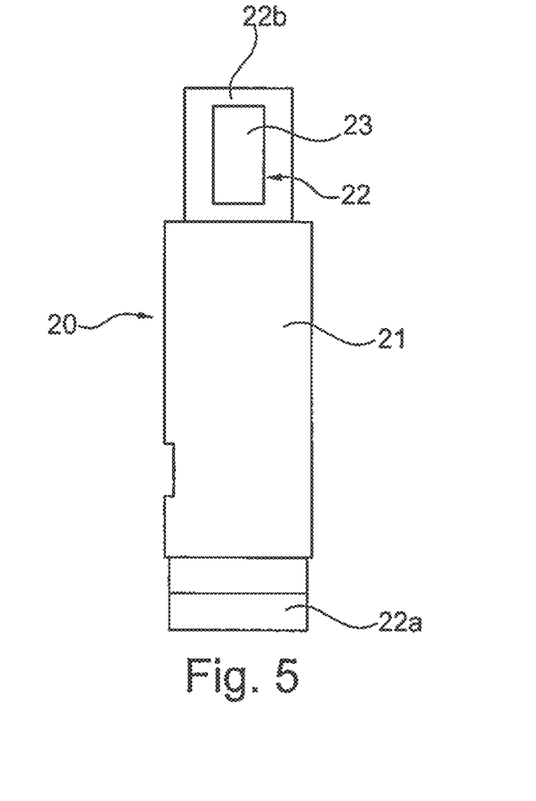
FIG. 5 shows a plant view of the sampling means which are part of the device according to the present invention.
Figure 6:
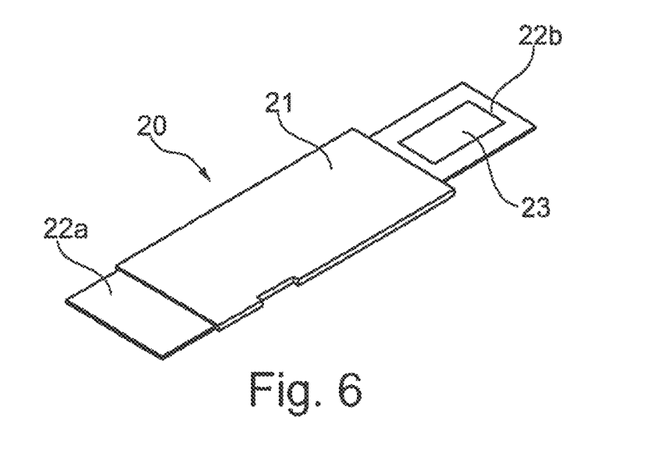
FIG. 6 shows a perspective view of the sampling means of FIG. 5.

According to FIGS. 5 and 6, the sampling means 20 in turn comprise a sheath 21 and a capturing scaffold capturing scaffold 22 associated to said filter sheath 21 and in turn supporting a capturing means 23.

According to a preferred embodiment of the present invention, the sampling means 20 comprises a sheath 21, a capturing scaffold 22 associated to said sheath 21, and a capturing means 23 associated to said capturing portion 24. More specifically, the sheath 21 is configured as a folder, and the capturing scaffold 22 is slidingly movable with respect to said sheath 21 between a resting position in which the capturing scaffold 22 is completely inserted into said sheath 21 and an operative position in which the capturing scaffold 22 is at least partially positioned outside said sheath 21 so that the capturing means 23 is completely exposed outside the sheath 21.

In order to provide the possibility to slide the capturing scaffold 22 with respect to the sheath 21, the capturing scaffold 22 extends outward the sheath 21 at the first end 22a, opposite to the second end 22b provided with the capturing means 23. The capturing scaffold 22 can therefore be handled by the user as will be better described in the following with reference to FIGS. 7 to 9.

Figure 7:
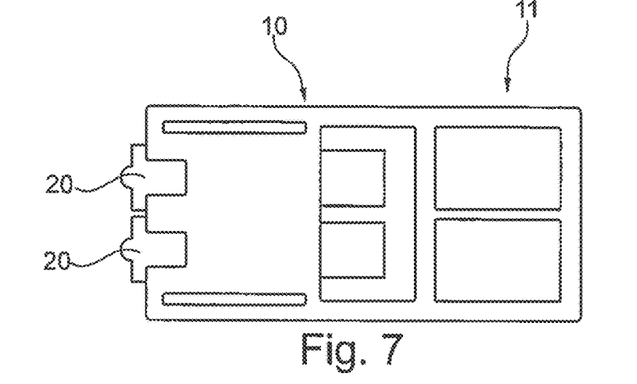
FIG. 7 shows a top view of the device according to the present invention, comprising the support frame and two sampling means inserted therein.

The device 10 according to an embodiment of the present invention comprising the support frame 11 and two sampling means 20 associated to said frame 11 is shown in FIG. 7.

Each of said sampling means 20 is inserted in one seat 13a provided on said support frame 11, and the capturing scaffold 22 of each of said sampling means 20 is in its operative position in which the capturing scaffold 22 is at least partially extracted from said sheath 21 so that the capturing means 23 is completely exposed outside the sheath 21, the capturing scaffold 22 projecting into the aperture 12 so that the capturing means 23 is entirely seeped through by the air flow which goes through the filtering unit 305.

Figure 8:
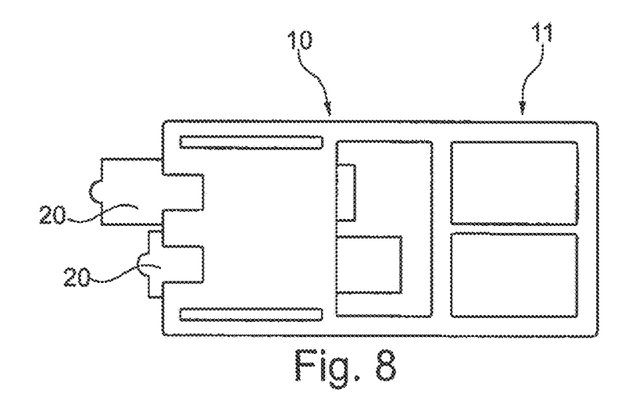
FIG. 8 shows the same view of FIG. 7 in which one of the two sampling means is partially extracted from the support frame.

With reference to FIG. 8, when the user wants to extract the samples from the frame, he can grasp the first end 22a of capturing scaffold 22 which projects outward from the sheath 21 and pull it outwardly thus obtaining that the second end 22b of the carrying element 22 slides into the sheath 21, the capturing scaffold 22 moving from its operative position to its resting position in which the membrane filter 23 is completely inserted into said sheath 21.

Figure 9:
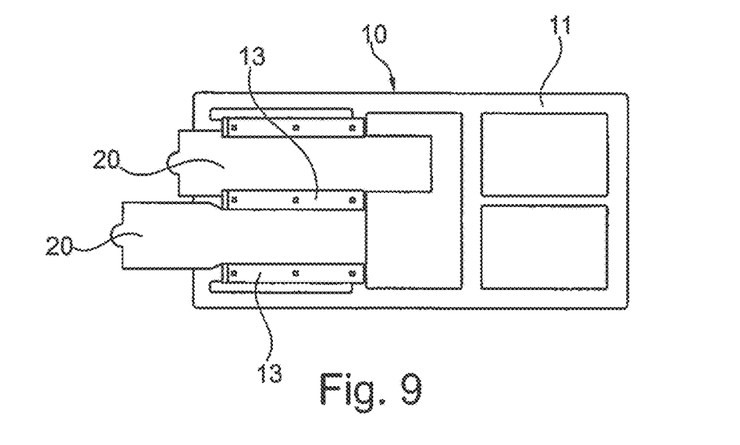
FIG. 9 represents the bottom view of the device of FIG. 8.
Figure 10:
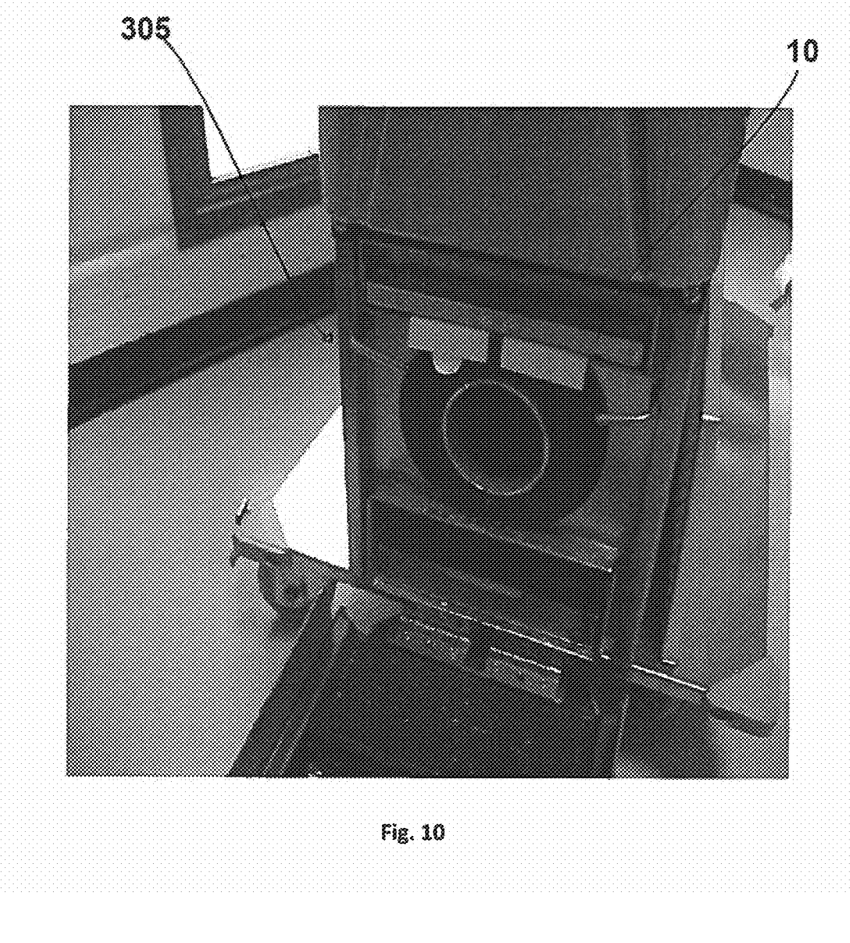
FIG. 10 represents a back view of the filtering unit of a ventilated shelving system according to the present invention.

FIG. 9 is a bottom view of FIG. 8.

Once the capturing scaffold 22 is in its resting position and the membrane filter 23 is completely inserted into said sheath 21, the first end 22a of the capturing scaffold 22 can be folded and secured to the sheath 21 in order to prevent unwanted movements of the capturing scaffold 22 itself.

According to a preferred embodiment of the present invention, the support frame 11 is made of metallic material, e.g. aluminum, steel, stainless steel and any other suitable material, while the sheath 21 and the capturing scaffold 22 are preferably made of cardboard, plastic or any other suitable, preferably disposable, material. Due to the possibility to completely insert the capturing scaffold 22 inside the sheath 21 before and after utilizing the sample means 20, it is assured that the capturing means 23 is fully protected before use and protected from contaminating particles.

In the same way, the possibility to completely retract the capturing scaffold 22 inside the sheath 21 when the user wants to extract the sampling means 20 from the frame 11 guarantees the safety of the operators while handling the samples.

A ventilated shelving storage system 100 for laboratory animals containment cages 200 comprising the device 10 is a further object of the present invention.

According to a preferred embodiment, the capturing scaffold 22 is inserted into the sheath 21 and is movable in a sliding manner with respect to the sheath 21 to a capturing position 25 located in the aperture 12, between a closed position in which said capturing portion 24 containing the capturing means 23 is completely inserted into the sheath 21 and an open position in which said capturing portion 24 containing the capturing means 23 is completely exposed to the air flow 500, comprising the area of the aperture 12 not covered by the capturing portion 24 and the flow passage area 14 of the ventilated shelving storage system 100.

In more detail, it is also part of the present invention a ventilated shelving storage system 100 for laboratory animals containment cages 200 comprising air guidance means 300 in turn comprising a filtering unit 305, the device 10 being removably associated to said filtering unit 305.

It is a further object of the present invention to provide a method for contamination-free removal of biological particles in a ventilated shelving storage system for laboratory animals containment cages.

The method according to an embodiment of the present invention comprises the following steps:
providing a ventilated shelving storage system 100 for laboratory animals containment cages 200 comprising air guidance means 300 in turn comprising a filtering unit 305;
providing a device 20 comprising a support frame 11 provided with at least one aperture 12, at least one sheath 21 removably associated to said support frame 11, at least one capturing scaffold 22 associated to said sheath 21, and at least one capturing means 23 associated to said at least one capturing scaffold 22;
positioning said at least one capturing scaffold 22 in an operative position in which the capturing scaffold 22 is at least partially extracted from said sheath 21 and projects into the aperture 12 of the support frame 11 so that said at least one capturing means 23 is entirely intercepted by (exposed to) the air flow which goes through the filtering unit 305.

According to the present invention, once the technician wants to extract the sample device from the filtering unit 305 the method comprises the following steps:
moving said capturing scaffold 22 from its open position to a closed position in which the capturing means 23 is completely inserted into said sheath 21;
removing the sheath 21 from the support frame 11 and then from the filtering unit 305.

In more detail, the method for contamination-free removal of biological samples particularly from unwanted organisms from a ventilated shelving storage system 100 for laboratory animals containment cages 200, comprises the following steps:
providing a sampling means 20 for said device 10,
positioning (moving) the sampling means 20 of said device 10 from the closed position to the open position collecting biological samples,
positioning (moving) the sampling means 20 of said device 10 from the open position to the closed position,
pulling off the sampling means 20 from the filtering unit 305,
transferring the sampling means 20 to a ventilated hood,
shifting the capturing scaffold 22 comprising the capturing means 23 to the open position,
transferring the capturing means 23 to a reaction vessel for analysis of biological samples of unwanted organisms, preferably by PCR.

Material obtained with the device is optionally further processed. For example, cells may be lysed, and the cell lysate may be separated and analyzed for characteristic components such as proteins or DNA. The biological material may be analyzed by methods well known to the person skilled in the art, for example, via amplification of pathogen-specific nucleic acid sequences by PCR; culture of pathogens on appropriate growth media, followed by isolation and either biochemical or histological assays; mass spectrometer-based detection of pathogen-specific components, such as MALDI-TOF; use of DNA hybridization techniques, such as for example Northern or Southern blot assays or hybridisation on DNA arrays as well as assays based on protein detection including but not limited to Ion Exchange Chromatography, Gel Filtration Chromatography, Affinity Chromatography, High Pressure Liquid Chromatography (HPLC) or immunoassays, such as enzyme-linked immunosorbent assays (ELISA), Western blot analysis or Immunoprecipitation.

Furthermore, a biosensor may be employed to detect the biological material. In theory a large number of these tiny biosensors would form an array capable of detecting any one of the known viruses, bacteria or parasites and would provide rapid identification as well as digital output to some controller or computer. Microbial biosensors would be designed with analytes that have a specificity for microbiological components such as surface components or specific metabolites. The mechanisms by which the microbes are detected could include electrochemical (amperometric, conductimetric or potentiometric) or electromagnetic (optical or mass) means.

In a preferred embodiment, pathogens are identified via amplification of pathogen-specific nucleic acid sequences. Methods of amplification of nucleic acid sequences include, for example, RT-PCR and its various modifications such as qRT-PCR (also referred to as Real Time RT-PCR). PCR is well known in the art and is employed to make large numbers of copies of a target sequence.

Due to the device 10 according to the present invention as above described, several advantages are therefore achieved. As it has been said, the device according to the present invention allows to perform sampling operations in a contamination-free way.

The device allows the operator to extract the sampling from the shelving system in a safe way at the same time preserving the membrane filter thus avoiding unwanted alteration of the sample.

Due to the structure of the device, and in particular of the support frame 11 which is preferably provided with a at least one flow passage 14, the air flow which goes through the filtering unit 305 is not negatively affected by the presence of the device 10.

Furthermore, the device according to the present invention can be easily associated to existing shelving systems, in particular to the filtering unit of already installed shelving systems, and therefore allows to retrofitting existing apparatuses.

Whilst the present invention has been clarified by means of the above description of the embodiments thereof as depicted in the drawings, the present invention is not limited to the embodiments as disclosed above and depicted in the drawings; the scope of the present invention is rather defined by the appended claims.

What is claimed is:

1. A device for contamination-free removal of biological samples from a ventilated shelving storage system for laboratory animals containment cages, comprising
    a support frame configured to be inserted into a filtering unit of the ventilated shelving storage system, the support frame comprising a planar plate having a seat portion and an aperture located therein adjacent the seat portion, wherein the aperture is positioned to receive a flow of air entering the filtering unit when the support frame is inserted into the filtering unit; and
    a sampling device configured to be removably inserted into the seat portion of the support frame, wherein the support frame is configured to receive the sampling device when the support frame is positioned in the filtering unit, the sampling device comprising:
        a capturing scaffold having a capturing device arranged within a capturing portion of the capturing scaffold; and
        a sheath associated to the capturing scaffold, wherein the capturing scaffold is inserted into the sheath and is movable in a sliding manner with respect to the sheath, when the sampling device is inserted into the support frame, to a capturing position located in the aperture of the support frame, wherein the capturing scaffold is further movable, when the sampling device is inserted into the support frame, between a closed position with the capturing portion completely inserted into the sheath and an open position with the capturing portion completely exposed to an air flow from an area of the aperture not covered by the capturing portion and a flow passage area of the ventilated shelving storage system.

2. The device according to claim 1, wherein the seat portion is configured for receiving the sampling device and supporting a portion of the sampling device that is not located over the aperture.

3. The device according to claim 1, wherein the seat portion for receiving the sampling device comprises a guiding structure for slidingly inserting the sampling device into the seat.

4. The device according to claim 3, wherein the guiding structure comprises a pair of straight and elongated guides.

5. The device according to claim 4, wherein the support frame further comprises at least one flow passage area.

6. The device according to claim 5, wherein the sheath and the capturing scaffold are made of a disposable material.

7. A ventilated shelving storage system for laboratory animals containment cages comprising:
    a load-bearing structure for supporting a plurality of cages and an air guidance device comprising a filtering unit; and
    a biological sample removal device comprising:
        a support frame configured to be inserted into the filtering unit of the ventilated shelving storage system, the support frame comprising a planar plate having a seat portion and an aperture located therein adjacent the seat portion, wherein the aperture is positioned to receive a flow of air entering the filtering unit when the support frame is inserted into the filtering unit; and
        a sampling device configured to be removably inserted into the seat portion of the support frame, wherein the support frame is configured to receive the sampling device when the support frame is positioned in the filtering unit, the sampling device comprising:
            a capturing scaffold having a capturing device arranged within a capturing portion of the capturing scaffold; and
            a sheath associated to the capturing scaffold, wherein the capturing scaffold is inserted into the sheath and is movable in a sliding manner with respect to the sheath, when the sampling device is inserted into the support frame, to a capturing position located in the aperture of the support frame, wherein the capturing scaffold is further movable, when the sampling device is inserted into the support frame, between a closed position with the capturing portion completely inserted into the sheath and an open position with the capturing portion completely exposed to an air flow from an area of the aperture not covered by the capturing portion and a flow passage area of the ventilated shelving storage system.

8. The ventilated shelving storage system according to claim 7, wherein the biological sample removal device is configured to be removably inserted into the filtering unit.

9. The ventilated shelving storage system according to claim 8, wherein the filtering unit comprises a containment case and the support frame of the biological sample removal device is configured to be inserted in a sliding manner into the containment case of the filtering unit.

10. The ventilated shelving storage system according to claim 7, wherein the filtering unit comprises a pre-filter and the biological sample removal device is inserted into the filtering unit adjacent the pre-filter.

11. A method for contamination-free removal of biological samples from a ventilated shelving storage system for laboratory animals containment cages the method comprising:
    providing a biological sample removal device comprising:
        a support frame configured to be inserted into a filtering unit of the ventilated shelving storage system, the support frame comprising a planar plate having a seat portion and an aperture located therein adjacent the seat portion, wherein the aperture is positioned to receive a flow of air entering the filtering unit when the support frame is inserted into the filtering unit; and
        a sampling device configured to be removably inserted into the seat portion of the support frame, wherein the support frame is configured to receive the sampling device when the support frame is positioned in the filtering unit, the sampling device comprising:
            a capturing scaffold having a capturing device arranged within a capturing portion of the capturing scaffold; and
            a sheath associated to the capturing scaffold, wherein the capturing scaffold is inserted into the sheath and is movable in a sliding manner with respect to the sheath, when the sampling device is inserted into the support frame, to a capturing position located in the aperture of the support frame, wherein the capturing scaffold is further movable, when the sampling device is inserted into the support frame, between a closed position with the capturing portion completely inserted into the sheath and an open position with the capturing portion completely exposed to an air flow from an area of the aperture not covered by the capturing portion and a flow passage area of the ventilated shelving storage system;

inserting the support frame into the filtering unit of the ventilated shelving storage system with the aperture positioned to receive the flow of air entering the filtering unit;

positioning the capturing scaffold of the sampling device in the open position;

collecting biological samples from unwanted organisms in the ventilated shelving storage system on the capturing device on the capturing scaffold of the sampling device;

positioning the capturing scaffold of the sampling device of the biological sample removal device in the closed position;

removing the sampling device from the support frame;

transferring the sampling device to a ventilated hood;

shifting the capturing scaffold, comprising the capturing device to the open position; and transferring the capturing device to a reaction vessel for analysis of the biological samples of the unwanted organisms.

12. The device according to claim 1, wherein the support frame comprises at least two seat portions configured to receive separate sampling devices.

* * * * *